US Patent

[19] Dattagupta et al.

[11] Patent Number: 4,777,129
[45] Date of Patent: * Oct. 11, 1988

[54] NUCLEIC ACID PROBE DETECTABLE BY SPECIFIC NUCLEIC ACID BINDING PROTEIN

[75] Inventors: Nanibhushan Dattagupta, New Haven; Peter M. M. Rae; William J. Knowles, both of Hamden; Donald M. Crothers, Northford, all of Conn.

[73] Assignee: Molecular Diagnostics, Inc., West Haven, Conn.

[*] Notice: The portion of the term of this patent subsequent to Feb. 2, 2005 has been disclaimed.

[21] Appl. No.: 662,858

[22] Filed: Oct. 19, 1984

Related U.S. Application Data

[63] Continuation-in-part of Ser. No. 560,462, Dec. 12, 1983.

[51] Int. Cl.$^4$ ............................................. C12Q 1/68
[52] U.S. Cl. .......................................... 435/6; 435/7; 435/34; 435/39; 436/501; 436/504; 436/508; 436/808; 436/811; 935/76; 935/77; 935/78
[58] Field of Search .................... 435/6, 7, 34, 39; 436/501, 504, 508, 808, 811; 935/76, 77, 78

[56] References Cited

U.S. PATENT DOCUMENTS 4,358,535 11/1982 Falkow et al. ........................ 435/34
4,395,486 7/1983 Wilson et al. ....................... 436/504
4,556,643 12/1985 Paau et al. ......................... 436/501
4,563,417 1/1986 Albarella et al. ...................... 435/6

FOREIGN PATENT DOCUMENTS 0079139 5/1983 European Pat. Off. .
0097373 1/1984 European Pat. Off. .
0131830 1/1985 Eurpean Pat. Off. .
0146815 7/1985 European Pat. Off. .
2125964 3/1984 United Kingdom .

OTHER PUBLICATIONS

Piette, et al., Proc. Natl. Acad. Sci. (U.S.A.), vol. 80, (1983), pp. 5540–5544.
Weber, et al., The Operon, Reznikoff, (ed.), Cold Spring Harbor Laboratory, 1980, pp. 155–175.
Salzman, et al., J. of Virol., vol. 30, No. 3, (1979), pp. 946–950.
Higuchi, et al., Proc. Natl. Acad. Sci. (U.S.A.), vol. 93, No. 9, (1976), pp. 3146–3150.
Annual Review of Biophysics and Bioengineering, vol. 10, 1981, "The Interaction of Intercalating Drugs with Nucleic Acids", Helen M. Berman and Peter R. Young, pp. 87–114.
Accounts of Chemical Research, vol. 11, 1978, "Platinum Complexes: Probes of Polynucleotide Structure and Antitumor Drugs", Stephen J. Lippard, pp. 211–217.
"Antibodies elicited against cis–diamminedichloroplatinum (II)–modified DNA are specific for cis–diamminedichloroplatinum (II)–DNA adducts formed in vivo and in vitro", M. C. Poirier et al., Proc. Natl. Acad. Sci. U.S.A. 79 (1982), pp. 6443–6447.

Primary Examiner—Robert J. Warden
Assistant Examiner—Stephen C. Wieder
Attorney, Agent, or Firm—Sprung Horn Kramer & Woods

[57] ABSTRACT

A nucleic acid detection probe comprising a hybridizable single stranded portion of nucleic acid connected with a non-hybridizable, single or double stranded nucleic acid portion, the non-hybridizable portion preferably including a recognition site for binding by a particular protein. Such recognition site can be a region of singly or doubly stranded nucleic acid specific for a particular nucleic acid binding protein such as lac repressor protein or can be a modified nucleic acid region such as a unique antigenic determinant introduced by interaction of the region with a modifier compound such as an intercalating agent or a platinum-containing ligand. The probe-binding protein can be labeled for ease of detection and in the case of an antigenic determinant binding site can be labeled antibody.

45 Claims, 1 Drawing Sheet

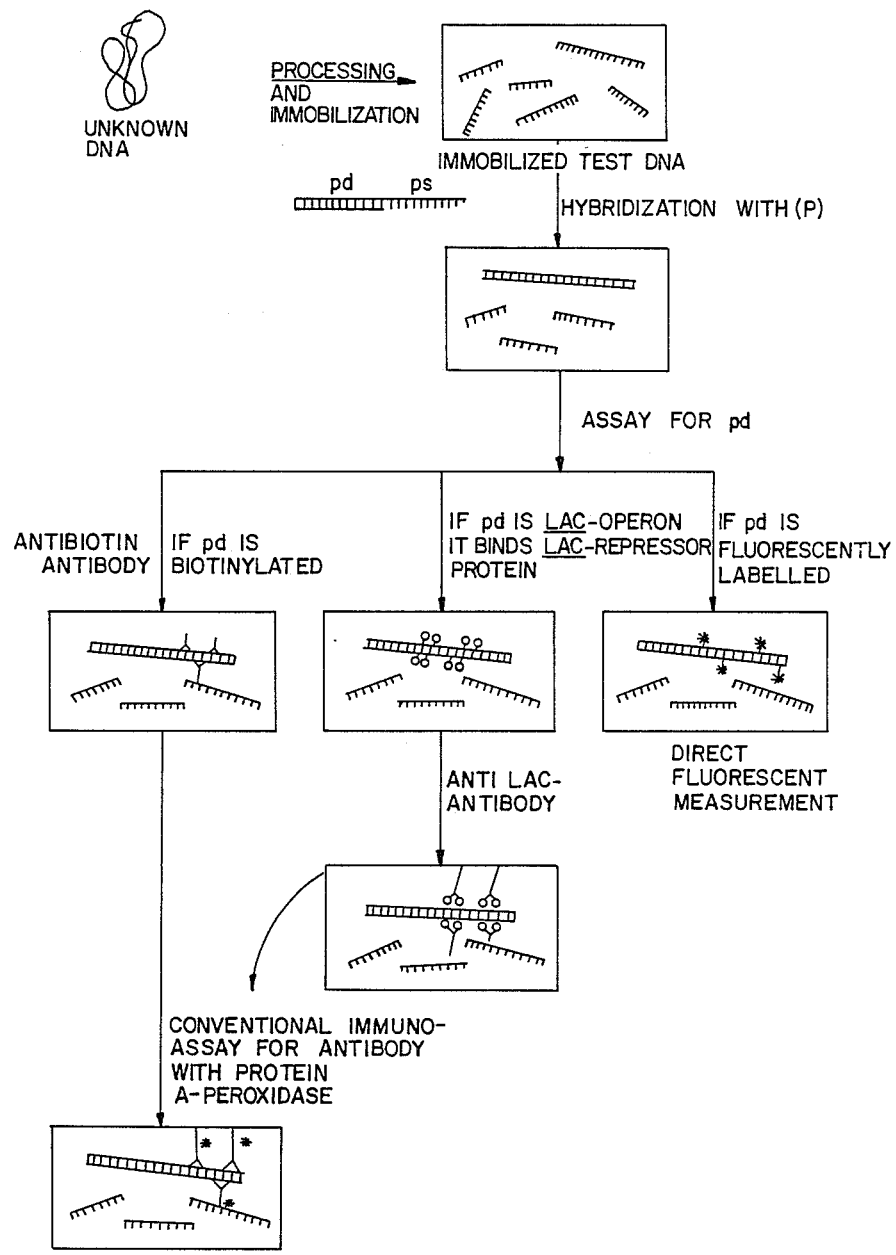

NUCLEIC ACID PROBE DETECTABLE BY SPECIFIC NUCLEIC ACID BINDING PROTEIN

This is a continuation-in-part of application Ser. No. 560,462, filed Dec. 12, 1983, now pending.

This application relates to a labeled nucleic acid probe suitable for analytical and diagnostic purposes with regard to genetic constitution, and particularly applicable to hybridization assays to detect specific polynucleotide sequences.

The evaluation of nucleic acid hybridizations is usually accomplished by detecting radioactivity introduced into a DNA:DNA or DNA:RNA hybrid via one member of a pair of complementary polynucleotides (the labeled member being designated the probe). Radiolabeling of the probe is effected by in vivo or in vitro polymerization of RNA or DNA under conditions in which precursors are isotopically tagged with $^3H$, $^{14}C$, $^{125}I$ or $^{32}P$, although it is also possible to label polynucleotides postsynthetically using $^{125}I$ or $^{32}P$-ATP. Each kind of radiolabeling has limitations, such as sensitivity of detection, isotope half-life and hazard, and it is highly desirable that probe labeling be accomplished without resort to radioactivity.

Available alternatives are (i) the attachment of haptens such as biotin to nucleic acid precursors, in which case an investigator is required to carry out in vitro polynucleotide syntheses in order to label a probe, then to detect the presence of biotinylated probe in a hybrid through the application of two or more steps; and (ii) the attachment of enzymes to oligonucleotide or polynucleotide probes, in which case, hybrids are detected by their ability to convert a substrate to an optically or chemically distinguishable product. Both of these alternatives to radioactivity involve moderate to substantial changes in the chemical structure of probes, so that qualitative and/or quantitive effects on hybridization are a possibility, if not a reality.

Application Ser. No. 511,063, filed July 5, 1983, discloses a dual hybridization assay conducted with a known and an unknown nucleic acid sample and a nucleic acid-containing detection probe.

U.S. patent application Ser. No. 511,063 describes a method for determining whether a nucleic acid in a test sample includes a particular nucleic acid sequence. Such method comprises the steps of:

(a) extracting the nucleic acids from a test sample, (b) digesting the extracted nucleic acids with a restriction enzyme thereby to effect restriction or not to effect restriction, depending on whether or not the restriction enzyme recognition site is precisely present in a sequence in the test DNA, (c) treating the product of (b) to form single-stranded nucleic acids, (d) contacting the single-stranded nucleic acids produced in (c) with first and second polynucleotide probes which are complementary to respective first and second portions of said sequence to be detected, the two portions being non-overlapping and immediately adjacent to the restriction site in question, and such contact being performed under conditions favorable to hybridization of said first and second probes to said sequence to be detected, hybridization with both of said probes to a test molecule being dependent upon whether in step (b) restriction did not occur, said first probe being incorporated with a distinguishable label, (e) separating, by means of said second probe, (i) any resulting dual hybridization product comprising said sequence to be detected hybridized to both said labeled first probe and said second probe, from (ii) any unhybridized and singly hybridized labeled first probe, and (f) by means of said label detecting any of said separated dual hybridization product which may be present.

U.S. patent applicaton Ser. No. 511,063 also describes a suitable kit for running the test, which comprises (i) first and second probes each including nucleic acid sequences present in the nucleic acid of a test sample, the first probe carrying a distinguishable label and being soluble in a liquid in which the determination will be run, the second probe being fixed on a solid support, and (ii) a restriction enzyme which will cleave the test sample or fail to depending on the presence or absence of a particular nucleic acid sequence at the point separating sequences complementary to the first and second probes, whereby a positive determination test sample (no cleavage at the point) is capable of hybridizing with both the first and second probes so as thereby to affix the label to the solid support for subsequent reading. The presence of labelling material on the solid support is an index of the extent of dual hybridization.

The first and second probes ar themselves formed in a special way. For example, a cloned beta-hemoglobin gene is digested by restriction enzymes which subdivide it into a number of fragments. In the case of detection of the sickle cell defect, the two of interest are a 340 bp (base pair) unit and a 201 bp unit. The fragments are separated from one another by subcloning, and one of them the 340 bp unit fragment, is fixed to a solid support such as a nitrocellulose sheet or disc, constituting the fixed probe. The other fragment is labeled either with a radioactive group, or a chemically detectable group such as a modified base or a visually detectable group such as one which fluoresces or has characteristic absorbance of ultraviolet or infrared light.

A key to the procedure, in the difference between an affected and unaffected test sample, is that in one of them, upon treatment with a restriction enzyme, there will be fragments longer than each probe so as to be capable of hybridizing with both the fixed probe and the labeled probe whereas the other will not have such longer units, so it will be incapable of hybridizing with both. The dual hybridization is the key to attaching the label to the solid support via one test sample but not the other, such support being what is ultimately analyzed for the presence of label.

With sickle cell anemia as an example, a normal hemoglobin gene can be used to make probes of 340 and 201 bp, and sickle cell anemia hemoglobin DNA, upon digestion, will have a long fragment which covers the two and can dually hybridize, while similarly treated normal DNA will have no such fragment.

The manner of enzymatically digesting the DNA material for producing the probes and/or treating the test samples in known in the art, as are methods for the various separations.

Advantageously, the known sample, the separation probe, is immobilized on a solid support and contacted with the unknown and the instant labeled detection probe. The contact is performed under conditions favorable to hybridization. A portion of the unknown nucleic acid hybridizes with the immobilized probe. If the unknown also contains a nucleotide sequence which is complementary to the nucleotide sequence of the detection probe, a second or dual hybridization will then take place by which the detection probe becomes affixed to the solid support. If the unknown nucleic acid lacks the particular complementary nucleotide sequence, the detection probe will not hybridize therewith. Accordingly, the extent of the second hybridization, as indicated by the extent of labeling, is an indicator of the presence of the particular nucleotide sequence of interest in the unknown.

It then becomes necessary to determine how much of the second hybridization has taken place, i.e., how much of the detection probe is on the immobilized support.

The detection probe can be labeled with various labels which can be detected in systems that measure specific binding activity, fluorescence or enzyme activity. Such labels include radioisotopes, fluorescent radicals, enzymes and haptens. If too many labels are provided as in the case of fluorophores, they may interfere with the second hybridization. On the other hand, if there are too few labels, assay is less sensitive.

It is, accordingly, an object of the present invention to provide a detection probe (or the probe carrying the labels) which can be used in an assay without the disadvantages of radioactivity and without chemical modification of the probe components which could interfere with hybridization.

It is another object of the invention to provide a means of labeling a probe with a large number of readable labels resulting in relatively high sensitivity, without interfering with hybridization.

These and other objects and advantages are realized in accordance with the present invention pursuant to which there is provided a detection probe comprising a hybridizable single stranded portion of nucleic acid which can hybridize with the unknown, connected with a non-hybridizable single or double stranded nucleic acid portion, the non-hybridizable portion advantageously including a recognition or binding site for a particular protein. If the non-hybridizable portion is double stranded, one of the strands may be continuous, i.e., covalently associated, with the hybridizable portion.

The hybridizable portion of nucleic acid can be any of those described in greater detail with regard to the detection probe of application Ser. No. 511,063, supra, as for example, a nucleotide sequence which is complementary to the genomic sequence responsible for sickle cell anemia.

The nucleic acid of the non-hybridizable portion can be a natural DNA sequence or synthetic oligonucleotide which contains a highly specific binding site or sites for a protein or proteins. A variety of nucleic acid binding site/binding protein pairs can be used in the present invention. One class of useful binding proteins are those known in biological systems to recognize specific polynucleotide sequences such as repressor proteins. Another class are antibodies which can bind to immunogenically altered nucleic acids.

In a preferred embodiment, the non-hybridizable portion can be specific for lactose (hereinafter referred to as lac) repressor protein which binds to an operator locus in the non-hybridizable portion, which operator must be double stranded, preferably after hybridization, as hybridization might sever the bond between operator and repressor. Accordingly, if the now-immobilized detection probe is contacted with a solution containing lac repressor protein, that protein will be selectively removed from the solution and will bind to the lac operator. Even if the concentration of nonspecific DNA in the hybridized sample is 1000-fold excess, the binding to nonspecific sequences is negligible. In living cells, repressor proteins bind to their corresponding operator sequences to modulate transcription of a gene. When an operator sequence is covalently attached to other sequences, binding of repressor proteins is still specific for the operator.

In another preferred embodiment, the non-hybridizable portion of the probe is chemically and/or physically modified to create a protein recognition site, for example, by interaction of a modifier compound which introduces a unique antigenic determinant into the non-hybridizable portion. Such modifier compounds are exemplified by intercalating agents and platinum-containing ligands. Intercalating agents interact with double stranded nucleic acids by becoming noncovalently inserted between base pairs. Such insertion causes the tertiary structure of the helix to change by unwinding and elongation along the helical axis. The resulting intercalation complex is characterized by newly formed antigenic determinants which are understood to comprise the intercalated compound and the reoriented phosphodiesterase backbones of the respective strands of the duplex. Useful intercalating agents are generally planar, aromatic organic molecules as exemplified by the acridine dyes, e.g., acridine orange, the phenanthridines, e.g., ethidium, the phenazines, furocoumarins, phenothiazines, and quinolines. Essentially any compound which will bind to single or double stranded nucleic acid to induce an immunogenic change can be used as the modifier compound.

The invention is applicable to all conventional hybridization assay formats. In particular, the unique detection probe of the present invention can be used in solution and solid-phase hybridization formats, including, in the latter case, formats involving immobilization of either sample or probe nucleic acids and sandwich formats. In general, the present invention provides a method for detecting a particular polynucleotide sequence in a test medium containing single stranded nucleic acids, comprising the step of (a) combining the test medium with a nucleic acid detection probe comprising at least one hybridizable single stranded base sequence which is substantially complementary to the sequence to be detected and a non-hybridizable double stranded portion having a recognition site for binding by a particularly protein, under conditions favorable to hybridization between the sequence to be detected and the complementary hybridizable sequence in the probe, (b) separating the solid support carrying hybridized probe from unhybridized probe, and (c) adding to the separated solid support carrying hybridized probe, the particular protein which binds the recognition site on the non-hybridizable portion of the probe and determining the protein which becomes bound to the solid support.

In one such assay for the presence of a particular nucleic acid nucleotide sequence in a sample, either the sample or a separation probe is immobilized on a support and, with a detection probe as described hereinabove, is subjected to hybridization, thereby affixing the non-hybridizable portion to the support. A protein is bound to the protein recognition site and thereby to the support. The protein is labeled at any stage, either before or after binding, and finally the label is assayed.

In another assay, after binding the protein and separating the support from the balance of the material, the support is treated in order to dissociate the protein from the hybridized detection probe and the dissociated protein is then assayed as by reading a label thereon, the label having been applied at any prior stage.

The invention is further described with reference to the accompanying drawing which is a schematic flow sheet of a hybridization and assay in accordance with the present invention.

Referring now more particularly to the drawing, the unknown DNA (to be tested) is processed as by digestion with a restriction enzyme, electrophoretic separation, southern transfer and/or simple denaturation. If not already immobilized, the DNA is then adsorbed on to a solid support (e.g., nitrocellulose paper) directly or by hybridization to a separation probe. The immobilized DNA is hybridized with a known probe. The known probe (P) has two regions. The region ps is single stranded and complementary to a specific gene to be detected and the region pd is a piece of double or single stranded, non-homologous DNA which carries the labels by which the labeling reaction will be detected. The pd region can be a specific sequence of double stranded DNA which binds a specific protein. For example, the double stranded DNA can be the lac promoter/operator sequence and then the protein is lac repressor. The pd region can also be a binding site for a specific antibody. The pd region can also be a specific single stranded, immunogenic polynucleotide sequence or poly [d(G-C)] which, when treated with high salt, changes its structure and becomes immunogenic in the Z form. The pd portion can also be modified with intercalating agents or platinum-containing DNA binding ligands to produce immunogenic sites.

If pd is the lac promoter/operator sequence, pd will bind lac repressor protein after the hybridization. The protein can then be assayed by an antibody or by direct labeling. The double stranded pd portion can also be modified with hapten, e.g., biotin. Then the biotinylated hybrid can be detected in a known manner. The pd portion can also be modified with a number of fluorophores and can be assayed directly.

In a specific embodiment involving a lac operator-repressor system, the foregoing process involves at least the following four steps:

Step I: Grow bacteria and isolate lac repressor protein;

Step II: Covalently couple the detection probe to lac operator DNA and clone the adduct to have a large quantity of sample;

Step III: Prepare lac repressor-FITC or lac repressor-$\beta$-galactosidase adduct or anti-lac repressor antibody;

Step IV: Hybridization and detection of lac operator via label on the lac repressor.

Thereafter, the amount of bound lac repressor protein can be assayed in various ways. For example, antibodies thereto can be contacted with the bound lac repressor and protein A conjugated with an enzyme can be bound to the antibodies. The amount of bound enzyme can then be determined by the enzyme's catalytic reaction of its substrate in a conventional manner.

The amount of enzyme indicates the amount of lac repressor which, in turn, indicates the amount of hybridization which occurred earlier. Alternatively, the lac repressor protein can be fluorescently labeled or labeled with enzyme and read in a conventional manner.

The double stranded region of the detection probe can also be specific for galactose repressor proteins, lambda repressor protein, catabolite gene activator protein, CAP, Cro protein and the like. The foregoing description for assay of bound lac repressor protein applies equally to assay for the presence of these proteins. Such proteins can be purified from strains of *Escherichia coli*. The DNA sequences to which these proteins bind have been identified and isolated using recombinant DNA technology. The segment of *E. coli* DNA that contains the lac repressor binding site (the lac promoter operator region) is transferred to recombinant plasmids that include segments of human DNA, such as portions of the gene encoding hemoglobin. These can be used without further genetic engineering to test for a number of hemoglobinopathies, such as some thalassemias and sickle-cell hemoglobinemia. Alternatively, in the dual hybridization scheme, two plasmids are used to determine if a sample of DNA from a human subject contains the genetic condition responsible for sickle cell hemoglobinemia. One plasmid is designated the separation probe. It contains DNA that is one flank of the dimorphic restriction enzyme cleavage site; it is immobilized as single stranded molecules on a solid support, and it is unlabeled. The second plasmid is designated the detection probe. It contains DNA that is the other flank of the dimorphic restriction site, and it has also been engineered to contain a segment of *E. coli* DNA that contains the lac promoter/operator region. Through the use of appropriate enzymes, the detector plasmid is made partially single stranded to the extent that $\beta$-globin gene sequences are available for hybridization while lac repressor recognition sites remain double stranded and available for protein binding.

Read out involving lac repressor protein provides highly specific recognition of the presence of the detection probe. It also opens a new set of possibilities for solution phase read out, because it is possible to release the repressor-antibody complexes from the operator DNA by addition of a $\beta$-galactoside, such as isopropylthio-galactoside. This allows automated batch or flow system processing.

In the foregoing description, the double stranded nucleic acid sequence contained a protein recognition site from the outset. However, if it did not contain such a site initially, it is possible to modify the DNA to create protein or antibody recognition sites for ease of reaction and detection.

Such modification can be effected by contact with intercalating agents, such as furocoumarins, e.g., angelicins, psoralens, etc., as described more fully in application Ser. No. 513,932, filed July 14, 1983, now pending.

The most efficient and sensitive method of detection of nucleic acids such as DNA after hybridization requires radioactively labelled DNA. The use of autoradiography and enzymes make the assay time consuming and requires experienced technical people. Recently, a non-radioactive method of labelling DNA has been described by Ward et al; they use the method of nick translation to introduce biotinylated U reside to DNA replacing T. The biotin residue is then assayed with antibiotin antibody or an avidin containing system. The detection in this case is quicker than autoradiography but the method of nick translation is a highly skilled art. Moreover, biotinylation using biotinylated UTP works only for thymine-containg polynucleotides. Use of other nucleotide triphosphates is very difficult because the chemical derivatization of A or G or C (containing —NH₂) with biotin requires elaborate techniques and highly skilled organic chemists.

U.S. patent application Ser. No. 513,932 describes labelling a nucleic acid by means of photochemistry, employing a photoreactive furocoumarin of phenanthridinium compound to link the nucleic acid to a label which can be "read" or assayed in a convention manner. The end product is thus a labeled nucleic acid probe comprising (a) a nucleic acid component, (b) a furocoumarin or phenanthridinium compound photochemically linked to the nucleic acid component, and (c) a label chemically linked to (b).

The photochemical method described in Ser. No. 513,932 provides more favorable reaction conditions than the usual chemical coupling method for biochemically sensitive substances. By using proper wavelengths for irradiation, DNA, RNA and proteins can be modified without affecting the native structure of the polymers. By coupling the indicated photoactive agents to the substrate, the latter can be photochemically reacted to the desired system.

To produce specific and efficient photochemical products, it is desirable that the chemicals interact in the dark in a specific manner.

For coupling to DNA, aminomethyl psoralen, and aminomethyl angelicin and amino alkyl ethidium or methidium azides are the preferred compounds. They bind to double-stranded DNA and only the dark complex produces photoadduct. If the photoadduct of DNA has to undergo nucleic acid hybridization, the DNA should be denaturable. In that case, conditions are employed so that simultaneous interaction of two strands of DNA with a single photoadduct is prevented. It is also desirable that the number of modification sites is not more than one per hundred nucleotide bases. Angelicin derivatives are superior to psoralen compounds for monoadduct formation. If a single-stranded probe is covalently attached to some extra double-stranded DNA, use of phenanthridinium and psoralen compounds is desirable since these compounds interact specifically to double-stranded DNA in the dark.

The nucleic acid component can be singly or doubly stranded DNA or RNA or fragments thereof such as are produced by restriction enzymes or even relatively short oligomers.

The link (b) can be a furocoumarin such as angelicin (isopsoralen) or psoralen or derivatives thereof which photochemically will react with nucleic acids, e.g., 4'-aminomethyl-4,5'-dimethylangelicin and 4'-aminomethyltrioxsalen (4'-aminomethyl-4,5', 8-trimethylpsoralen). It can also be a mono- or bis-azido aminoalkyl methidium or ethidium compound.

The label can be anything which can be assayed in known manner, e.g., a hapten such as biotin, an enzyme such as beta-galactosidase or horseradish peroxidase, papain, or a phycobiliprotein.

The individual reactions and reaction conditions are more-or-less well know. Advantageously, the link (b) is first combined with the label chemically and thereafter combined with the nucleic acid component. For example, since biotin carries a carboxyl group, it can be combined with the furocoumarin by way of amide or ester formation without interferring with the photochemical reactivity of the furocoumarin or the biological activity of the biotin. Other aminomethylangelicin, psoralen and phenanthridinium derivatives can be similarly reacted, as can phenanthridinium halides and derivatives thereof such as aminopropyl methidium chloride.

Alternatively, a bifunctional reagent such as dithiobis succinimidyl propionate or 1,4-butanedioldiglycidyl ether can be used directly to couple the photochemically reactive molecule with the label where the reactants have alkyl amino residues, again in a known manner with regard to solvents, proportions and reaction conditions.

Certain bifunctional reagents such as glutaraldehyde re not suitable because, while they couple, they modify the nucleic acid and thus interfere with the assay.

The particular sequence in making the test material can be varied. Thus, for example, an amino-substituted psoralen can first be photometrically coupled with a nucleic acid, the product having pendant amino groups by which it can be coupled to the label. Alternatively, the psoralen can first be coupled to the enzyme and then to the nucleic acid.

If the label is an enzyme, for example, the product will ultimately be placed on a suitable medium and the extent of catalysis will be determined. Thus, if the enzyme is a phosphatase, the medium could contain nitrophenyl phosphate and one would monitor the amount of nitrophenol generated by observing the color. If the enzyme is beta-galactosidase, the medium can contain o-nitrophenyl-D-galacto-pyranoside which also will liberate nitrophenol.

The art is aware of other labels and how to test for their presence, e.g., for a biotin label use an avidin test, for histones use FITC, if there is free —NH₂ moiety one can directly post-label with FITC, etc.

Platinum-containing ligands can be similarly employed. The reagents render the non-hybridizable nucleic acid portion recognizable by protein. If the non-hybridizable portion is rendered immunogenic, such protein can be an antibody, i.e., an immunoglobulin, for example, a monoclonal antibody. The antibody can be bound to the non-hybridizable portion in an amount corresponding to the amount of furocoumarin creating the protein recognition sites. Antibody recognition sites can also be created when pd contains poly [d(G-C)] sequences, and the probe is exposed to high salt concentration.

In the case where the modifier compound is an intercalating agent, such compound preferably is a low molecular weight, planer, usually aromatic but sometimes polycyclic, molecule capable of binding with double stranded nucleic acids, e.g., DNA/DNA, DNA/RNA, or RNA/RNA duplexes, usually by insertion between base pairs. The primary binding mechanism will usually be noncovalent, with covalent binding occurring as a second step where the intercalator has reactive or activatable chemical groups which will form covalent bonds with neighboring chemical groups on one or both of the intercalated duplex strands. The result of intercalation is the spreading of adjacent base pairs to about twice their normal separation distance, leading to an increase in molecular length of the duplex. Further, unwinding of the double helix of about 12 to 36 degrees must occur in order to accommodate the intercalator. General reviews and further information can be obtained from Lerman, J. Mol. Biol. 3: 18(1961); Bloomfield et al, "Physical Chemistry of Nucleic Acids", Chapter 7, pp. 429–476, Harper and Rowe, NY(1974); Waring, Nature 219: 1320 (1968); Hartmann et al, Angew. Chem., Engl. Ed. 7: 693(1968); Lippard, Accts. Chem. Res. 11: 211(1978); Wilson, Intercalation Chemistry (1982), 445; and Berman et al, Ann. Rev. Biophys. Bioeng. 10: 87(1981).

A wide variety of intercalating agents can be used in the present invention. Some classes of these agents and examples of specific compounds are given in the following table:

| Intercalator Classes and Representative Compounds | Literature References |
|---|---|
| A. Acridine dyes | Lerman, J., supra; Bloomfield et al, supra; |
| proflavin, acridine orange, quinacrine, acriflavine | Miller et al, Biopolymers 19:2091(1980) |
| B. Phenanthridines | Bloomfield et al, supra; |
| ethidium | Miller et al, supra |
| coralyne | Wilson et al, J. Med. Chem. 19:1261(1976) |
| ellipticine, ellipticine cation and derivatives | Festy et al, FEBS Letters 17:321(1971); Kohn et al, Cancer Res. 35:71(1976); LePecq et al, PNAS (USA)71: 5078(1974); Pelaprat et al, J. Med. Chem. 23:1330(1980) |
| C. Phenazines | Bloomfield et al, supra |
| 5-methylphenazine cation | |
| D. Phenothiazines | " |
| chlopramazine | |
| E. Quinolines | " |
| chloroquine | |
| quinine | |
| F. Aflatoxin | " |
| G. Polycyclic hydrocarbons and their oxirane derivatives | " |
| 3,4-benzopyrene, benzopyrene diol epoxide, 1-pyrenyl-oxirane | Yang et al, Biochem. Biophys. Res. Comm. 82:929(1978) |
| benzanthracene-5,6-oxide | Amea et al, Science 176:47(1972) |
| H. Actinomycens | Bloomfield et al, supra |
| actinomycin D | |
| I. Anthracyclinones | " |
| β-rhodomycin A | |
| daunamycin | |
| J. Thiaxanthenones | " |
| miracil D | |
| K. Anthramycin | " |
| L. Mitomycin | Ogawa et al, Nucl. Acids Res., Spec. Publ. 3:79(1977); Akhtar et al, Can. J. Chem. 53:2891(1975) |
| M. Platinum Complexes | Lippard, Accts. Chem. Res. 11:211(1978) |
| N. Polyintercalators | Waring et al, Nature 252:653(1974); Wakelin, Biochem. J. 157:721(1976) |
| echinomycin | |
| quinomycin | Lee et al, Biochem. J. 173:115(1978); Huang et al, Biochem. 19: 5537(1980): Viswamitra et al, Nature 289: 817(1981) |
| triostin | |
| BBM928A | |
| tandem | |
| diacridines | LePecq et al, PNAS (USA)72:2915(1975): Carrellakis et al, Biochim. Biophys. Acta 418:277(1976); Wakelin et al, Biochem 17:5057(1978); Wakelin et al, FEBS Lett. 104:261(1979); Capelle et al, Biochem. 18:3354(1979); Wright et al, Biochem. 19:5825(1980); Bernier et al, Biochem. J. 199:479 (1981); King et al, Biochem. 21:4982(1982) |
| ethidium dimer | Gaugain et al, Biochem. 17:5078(1978); Kuhlman et al, Nucl. Acids Res. 5:2629(1978); Marlcovits et al, Anal. Biochem. 94:259(1979): Dervan et al, JACS 100:1968(1978); ibid 101:3664(1979). |
| ellipticene dimers and analogs | Debarre et al, Compt. Rend. Ser. D. 284: 81(1977); Pelaprat et al, J. Med. Chem. 23:1336(1980) |
| heterodimers | Cain et al, J. Med. Chem. 21:658(1978); Gaugain et al, Biochem. 17:5078(1978) |
| trimers | Hansen et al, JCS Chem. Comm. 162(1983); Atnell et al, JACS 105:2913(1983) |
| O. Norphillin A | Loun et al, JACS 104: 3213(1982) |
| P. Fluorenes and fluorenones | Bloomfield et al, supra |
| fluorenodiamines | Witkowski et al, Wiss. Beitr.-Martin-Luther-Univ. Halle Wittenberg, 11(1981) |
| Q. Furocoumarins | |
| angelicin | Venema et al, MGG, Mol. Gen. Genet. 179;1 (980) |
| 4,5'-dimethylangelicin | Vedaldi et al, Chem.-Biol. Interact. 36: 275(1981) |
| psoralen | Marciani et al, Z. Naturforsch B 27(2): 196(1972) |
| 8-methoxypsoralen | Belognzov et al, Mutat. Res. 84:11(1981); Scott et al, Photochem. Photobiol. 34:63(1981) |
| 5-aminomethyl-8-methoxypsoralen | Hansen et al, Tet. Lett. 22:1847(1981) |
| 4,5,8-trimethylpsoralen | Ben-Hur et al, Biochim. Biophys. Acta 331:181(1973) |
| 4'-aminomethyl-4,5,8-trimethylpsoralen | Issacs et al, Biochem. 16:1058(1977) |
| xanthotoxin | Hradecma et al, Acta Virol. (Engl. Ed.) 26:305(1982) |
| khellin | Beaumont et al, Biochim. Biophys. Acta 608:1829(1980) |
| R. Benzodipyrones | Murx et al, J. Het. Chem. 12:417(1975); Horter et al, Photochem. Photobiol. 20: 407(1974) |
| S. Monostral Fast Blue | Juarranz et al, Acta Histochem. 70:130(1982) |

Where desirable or particularly advantageous, the intercalating agent can be chemically linked, e.g., by covalent bonds, to one or both of the complementary strands in the intercalation complex. Essentially any available method cn be used to accomplish such linkage. Conveniently, the linkage is formed by effecting intercalation with a reactive, preferably photoreactive intercalator, followed by the linking reaction. A particularly useful method involves the use of azido-intercalators.

The reactive nitrenes are readily generated at long wavelength ultraviolet or visible light and the nitrenes of arylazides prefer insertion reactions over their rearrangement products [see White et al, Methods in Enzymol. 46: 644(1977)]. Representative azidointercalators are 3-azidoacridine, 9-azidoacridine, ethidium monoazide, ethidium diazide, ethidium dimer azide (Mitchell et al, JACS 104: 4265(1982)], 4-azido-7-chloro-quinoline, and 2-azidofluorene. Other useful photoreactable intercalators are the furocoumarins which form [2+2] cycloadducts with pyrimidine residues. Alkylating agents can also be used such as bis-chloroethylamines and epoxides or aziridines, e.g., aflatoxins, polycyclic hydrocarbon epoxides, mitomycin, and norphillin A.

Alternatively, the protein recognition site can be on a segment of the non-hybridizable portion other than nucleic acid per se. For example, the nucleic acid of the non-hybridizable portion can be linked by a member such as a furocoumarin to a chemical group such as biotin, the biotin constituting the protein recognition site.

The biotin can be assayed in a conventional manner, for example, with avidin or an anti-hapten antibody. The furocoumarin may be linked to a fluorophore, the fluorophore thereafter being assayed for fluorescence.

Labeling with the aforementioned proteins can be performed either before or after modification of the double stranded nucleic acid, preferably after.

Salts may also be used as a means of modifying the non-hybridizable portion to render it protein recognizable (e.g., poly [d(G-C)] or poly [d(G-$^{me}$C)] changes to Z-form). Suitable salts include sodium chloride, other alkali and alkaline earth metal soluble salts of mineral acids, spermine or spermidines, advantageously in concentrations of at least about 1% by weight. Advantageously, the solvent is water. Both the salt-modified nucleic acid and the furocouramin modified nucleic acid will be antigenic, e.g., will be capable of binding a specific antibody which can be assayed in conventional manner. For example, as hereinabove, the protein A can be conjugated with an enzyme which functions as the label in subsequent assay.

The probe will comprise at least one single stranded base sequence substantially complementary to or homologous with the sequence to be detected. However, such base sequence need not be a single continuous polynucleotide segment, but can be comprised of two or more individual segments interrupted by nonhomologous sequences. These nonhomologous sequences can be linear, or they can be self-complementary and form hairpin loops. In addition, the homologous region of the probe can be flanked at the 3'- and 5'-terminii by nonhomologous sequences, such as those comprising the DNA or RNA of a vector into which the homologous sequence had been inserted for propagation. In either instance, the probe as presented as an analytical reagent will exhibit detectable hybridization at one or more points which sample nucleic acids of interet. Linear or circular single stranded polynucleotides can be used as the probe element, with major or minor portions being duplexed with a complementary polynucleotide strand or strands, provided that the critical homologous segment or segments are in single stranded form and available for hybridization with sample DNA or RNA. Particularly preferred will be linear or circular probes wherein the homologous probe sequence is in essentially only single stranded form [see particularly, Hu and Messing, Gene 17: 271-277(1982)].

The binding of the particular protein reagent to the hybridization product in the present method can be detected by any convenient technique. Advantageously, the binding protein will itself be labeled with a detectable chemical group. Such detectable chemical group can be any material having a detectable physical or chemical property. Such materials have been well-developed in the field of immunoassays and in general most any label useful in such methods can be applied to the present invention. Particularly useful are enzymatically active groups, such as enzymes (see Clin. Chem.(1976)22: 1243), enzymes substrates (see British Pat. Spec. No. 1,548,741), coenzymes (see U.S. Pat. Nos. 4,230,797 and 4,238,565), and enzyme inhibitors (see U.S. Pat. No. 4,134,792); fluorescers (see Clin. Chem.(1979)25: 353); chromophores; luminescers such as chemiluminescers and bioluminescers (see Clin. Chem.(1979)25: 512, and ibid, 1531); specifically bindable ligands; and radioisotopes such as $^3$H, $^{35}$S, $^{32}$P, $^{125}$I, and $^{14}$C. Such labels and labeling pairs are detected on the basis of their own physical properties (e.g., fluorescers, chromophores and radioisotopes) or their reactive or binding properties (e.g., enzymes, substrates, coenzymes and inhibitors). For example, a cofactor-labeled binding protein can be detected by adding the enzyme for which the label is a cofactor and a substrate for the enzyme. A hapten or ligand (e.g., biotin) labeled binding protein can be detected by adding an antibody to the hapten or a protein (e.g., avidin) which binds the ligand, tagged with a detectable molecule. Such detectable molecule can be some molecule with a measurable physical property (e.g., fluorescence or absorbance) or a participant in an enzyme reaction (e.g., see above list). For example, one can use an enzyme which acts upon a substrate to generate a product with a measurable physical property. Examples of the latter include, but are not limited to, β-galactosidase, alkaline phosphatase and peroxidase. For in situ hybridization studies, ideally the final product is water insoluble. Other labeling schemes will be evident to one of ordinary skill in the art.

Alternatively, the binding protein can be detected based on a native property such as its own antigenicity. A labeled anti-(binding protein)antibody will bind to the primary protein reagent where the label for the antibody is any conventional label as above. Further, where the binding protein is an antibody, it can be detected by complement fixation or the use of labeled protein A, as well as other techniques known in the art for detecting antibodies.

The label will be linked to the binding protein by direct chemical linkage such as involving covalent bonds, or by indirect linkage such as by incorporation of the label in a micrrocapsule or liposome which is in turn linked to the binding protein. Labeling techniques are well-known in the art and any convenient method can be used in the present invention.

When the binding protein is an antibody, such reagent can consist of whole antibodies, antibody fragments, polyfunctional antibody aggregates, or in general any substance comprising one or more specific binding sites from an antibody. When in the form of whole antibody, it can belong to any of the classes and subclasses of known immunoglobulines, e.g., IgG, IgM, and so forth. Any fragment of any such antibody which retains specific binding affinity for the probe recognition site can also be employed, for instance, the fragments of IgG conventionally known as Fab, F(ab'), and F(ab')2. In addition, aggregates, polymers and conjugates of immunoglobulins or their fragments can be used where appropriate.

The immunoglobulin source for the antibody reagent can be obtained in any available manner such as conventional antiserum and monoclonal techniques. Antiserum can be obtained by well-established techniques involving immunization of an animal, such as a mouse, rabbit, guinea pig or goat, with an appropriate immunogen. The immunogen will usually comprise an ionic complex between a cationic protein or protein derivative (e.g., methylated bovine serum albumin) and the modified nucleic acid. Alternatively, the modified nucleic acid can be covalently coupled to a carrier protein. The immunoglobulins can also be obtained by somatic cell hybridization technique, such resulting in what are commonly referred to as monoclonal antibodies. The immunogen used for primary injections leading to hybridoma formation will be as described above.

The test sample to be assayed can be any medium of interest, and will usually be a liquid sample of medical, veterinary, environmental, nutritional, or industrial significance. Human and animal specimens and body fluids particularly can be assayed by the present method, including urine, blood (serum or plasma), milk, cerebrospinal fluid, sputum, fecal matter, lung aspirates, throat swabs, genital swabs and exudates, rectal swabs, and nasopharyngal aspirates. Where the test sample obtained from the patient or other source to be tested contains principally double stranded nucleic acids, such as contained in cells, the sample will be treated to denature the nucleic acids, and if necessary first to release nucleic acids from cells. Denaturation of nucleic acids is preferably accomplished by heating in boiling water or alkali treatment (e.g., 0.1N sodium hydroxide), which if desired, can simultaneously be used to lyse cells. Also, release of nucleic acids can, for example, be obtained by mechanical disruption (freeze/thaw, abrasion, sonication), physical/chemical disruption (detergents such as Triton, Tween, sodium dodecylsulfate, alkali treatment, osmotic shock, or heat), or enzymatic lysis (lysozyme, proteinase K, pepsin). The resulting test medium will contain nucleic acids in single stranded form which can then be assayed according to the present hybridization method.

As is known in the art, various hybridization conditions can be employed in the assay. Typically, hybridization will proceed at slightly elevated temperatures, e.g., between about 35° and 70° C. and usually around 65° C., in a solution comprising buffer at pH between about 6 and 8 and with appropriate ionic strength (e.g., 2XSSC where 1XSSC=0.15M sodium chloride and 0.015M sodium citrate, pH 7.0), protein such as bovine serum albumin, Ficoll (a trademark identifying a copolymer of sucrose and epichlorohydrin sold by Pharmacia Fine Chemicals, Piscataway, NJ), polyvinylpyrrolidone, and a denatured foreign DNA such as from calf thymus or salmon sperm. The degree of complementarity between the sample and probe strands required for hybridization to occur depends on the stringency of the conditions. The extend and specificity of hybridization is affected by the following principal conditions:

1. The purity of the nucleic acid preparation.
2. Base composition of the probe—G-C base pairs will exhibit greater thermal stability than A-T base pairs. Thus, hybridizations involving higher G-C content will be stable at higher temperatures.
3. Length of homologous base sequence—Any short sequence of bases (e.g., less than 6 bases), has a high degree of probability of being present in many nucleic acids. Thus, little or no specificity can be attained in hybridizations involving such short sequences. The present homologous probe sequence will be at least 10 bases, usually 20 bases or more, and preferably greater than 100 bases. From a practical standpoint, the homologous probe sequence will often be between 300–1000 nucleotides.
4. Ionic strength—The rate of reannealing increases as the ionic strengthh of the incubation solution increases. Thermal stability of hybrids also increases.
5. Incubation temperature—Optimal reannealing occurs at a temperature about 25°–30° C. below the melting temperature (Tm) for a given duplex. Incubation at temperatures significantly below the optimum allows less related base sequences to hybridize.
6. Nucleic acid concentration and incubation time—Normally, to drive the reaction towards hybridization, one of the hybridazable sample nucleic acid will be present in excess, usually 100 fold excess or greater.
7. Denaturing reagents—The presence of hydrogen bond disrupting agents suc as formamide and urea increases the stringency of hybridization.
8. Incubation time—The longer the incubation time the more complete will be the hybridization.
9. Volume exclusion agents—The presence of these agents, as exemplified by dextran and dextran sulfate, are thought to effectively increase the concentration of the hybridizing elements thereby increasing the rate of resulting hybridization.

Practice of the present analytical method is not limited to any particular hybridization format. Any conventional hybridization technique can be used. As improvements are made and as conceptually new formats are developed, such can be readily applied to carrying out the present method. Conventional hybridization formats which are particularly useful include those wherein the sample nucleic acids is immobilized on a solid support (solid-phase hybridization) and those wherein the polynucleotide species are all in solution (solution hybridization).

In solid-phase hybridization formats, sample polynucleotides are fixed in an appropriate manner in their single stranded form to a solid support. Useful solid support are well known in the art and include those which bind nucleic acids either covalently or non-covalently. Noncovalent supports which are generally understood to involve hydrophobic bonding include naturally occurring and synthetic polymeric materials, such as nitrocellulose, derivatized nylon, and fluorinated polyhydrocarbons, in a variety of forms such as filters or solid sheets. Covalent binding supports are also useful and comprise materials having chemically reactive groups or groups, such as dichlorotriazine, diazobenzyloxymethyl, and the like, which can be activated for binding to polynucleotides.

A typical solid-phase hybridization technique begins with immobilization of sample nucleic acids onto the support in single stranded form. This initial step essentially prevents reannealing of complementary strands from the sample and can be used as a means for concentrating sample material on the support for enhanced detectability. The polynucleotide probe is then contacted with the support and hybridization detected as described herein. The solid support provides a convenient means for separating labeled reagent associated with hybridized probe from that which remains unassociated.

Another method of interest is the sandwich hybridization technique wherein one of two mutually exclusive fragments of the homologous sequence of the probe is immobilized and the other is labeled. The presence of the polynucleotide sequence of interest results in dual hybridization to the immobilized and labeled probe segments, again with the same ultimate measurement of support-associated intercalation complexes. See Methods in Enzymology 65: 468(1080) and Gene 21: 77-85(1983) for further details.

The invention also extends to assays involving detection probes wherein the non-hybridizable portion has been modified to attach a protein recognition site, as with a furocoumarin, as a link between the non-hybridizable double or single strand component and the protein recognition site, which can be a hapten or ligand. An immobilized separation probe or test sample is subjected to hybridizing conditions in the presence of a detection probe so modified to bind a protein and carrying a label, and the label is assayed. Alternatively, the protein may constitute an antibody and the assayed immunologically in conventional manner, without formal labeling of the protein. As another alternative, if a hapten or ligand is at the the protein recognition site, its presence can be assayed. The furocoumarin can also link a fluorophore and the fluorophore utilized as the assayable element.

The detection probes made and used as described above exhibit greater sensitivity than heretofore by virtue of the far greater number of labels per single stranded nucleic acid probe molecule than is possible with directly-labeling the probe molecules.

The present invention additionally provides a reagent system, i.e., reagent combination or means, comprising all of the essential elements required to conduct a desired assay method. The reagent system is presented in a commercially packaged form, as a composition or admixture where the compatability of the reagents will allow, in a test device configuration, or more usually as a test kit, i.e., a packaged combination of one or more containers, devices, or the like holding the necessary reagents, and usually including written instructions for the performance of assays. Reagent systems of the present invention include all configurations and compositions for performing the various hybridization formats described herein.

In all cases, the reagent system will comprise (1) a probe as described herein and (2) the binding protein reagent, preferably labeled with a detectable chemical group also as described herein. The system can additionally comprise a solid support for immobilizing single stranded nucleic acids from the test medium. For a sandwich format, a second, separation, probe as described above is included in the system. A test kit form of the system can additionally include ancillary chemicals such as the components of the hybridization solution and denaturation agents capable of converting double stranded nucleic acids in a test sample into single stranded form. Preferably, there is included a chemical lysing and denaturing agent, e.g., alkali, for treating the sample to release single stranded nucleic acid therefrom.

The invention will be further described with reference to the accompanying examples wherein all parts are by weight unless otherwise expressed.

EXAMPLE 1

Step I—Isolating Lac Repressor Protein

*E. coli* strain BMH 461:

$\Delta$ (lac pro) ($\lambda$ $C_1$857t68d lac $i^qz^+y^-$)/(F' lac $i^qz^+y^-$ pro$^+$), developed by Muller-Hill et al., carries a thermally inducible lambda lysogen with a lac repressor gene and it overproduces the protein 1000-fold compared to the wild type strain. (Other *E. coli* strains can also be used to isolate the protein). The strain is grown substantially as described by Muller-Hill et al. and Platt et al. [Muller-Hill et al., *Proc. Natl. Acad. Sci.*, 59, 1259 (1968); Platt et al., in *Exp. in Mol Genetics* (ed., J. Miller) CSH, pp. 363-393 (1972)], as follows:

The cells are grown in a medium containing 3% Bactotryptone, 2% Bacto yeast extract (both from Difco) and 0.5% sodium chloride at 32° C. to an OD 550 of 3. Then the temperature is raised to 44° C. for 20 minutes to effect for 5 hours. The cells are collected from the culture by centrifugation at 6000 rpm and stored frozen at −80° C.

100 gms of cells are thawed and blended in a Waring blender and the supernatant after centrifugation is made up to 100 ml with a buffer comprising 0.2M Tris HCl, PH 6.9, 0.2M KCl, 10 mM mg acetate, 0.1 mM dithiothreitol, 5% (v/v glycerol) and precipitated by adding 0.23 g/ml ammonium sulfate. The precipitate is collected by centrifugation at 10,000 rpm and redissolved in 5 ml of the foregoing buffer and desalted by exhaustive dialysis against a buffer solution comprising 0.12M potassium phosphate (PH 7.4) 0.1 mM dithiothreitol, 5% (v/v) glycerol; 2% (v/v) dimethyl sulfate.

The lac repressor protein eluate is finally purified on a phosphocellulose column using phosphate buffer as above, with a linear gradient of 0.12 to 0.24 potassium phosphate.

The purity of the lac repressor-containing fraction is checked by SDS-polyacrylamide gel electrophoresis. The activity of the lac repressor protein is measured by its ability to bind operator-containing DNA in a known manner. The protein can be stored at −80° C. until use.

Step II—Covalently Coupling Detection Probe to Lac Operator DNA

Preparation of a plasmid having both multiple copies of the lac repressor protein binding site (lac operator) and a portion of the β-hemoglobin gene, pursuant to *Molecular Cloning*, Maniatis et al., Cold Spring Harbor Laboratory, 1982.

Maniatis et al describe the following: Cloning in Plasmids

In principle, cloning in plasmid vectors is very straightforward. The plasmid DNA is cleved with a restriction endonuclease and joined in vitro to foreign DNA. The resulting recombinant plasmids are then used to transform bacteria. In practice, however, the plasmid vector must be carefully chosen to minimize the effort required to identify and characterize recombinants. The major difficulty is to distinguish between plasmids that contain sequences of foreign DNA and vector DNA molecules that have recirculated without insertion of foreign sequences. Recirculation of the plasmid can be limited to some extend by adjusting the concentrations of the foreign DNA and vector DNA during the ligation reaction. However, a number of procedures, described below, have been developed either to reduce recircularization of the plasmid still further or to distinguish recombinants from nonrecombinants by genetic techniques.

Insertional Inactivation

This method can be used with plasmids that carry two or more antibiotic-resistance markers.

The DNA to be inserted and the purified plasmid DNA are digested with a restriction enzyme that, in this example, recognizes a unique site located in the plasmid with the tetracycline-resistance gene. After ligating the two DNAs at the appropriate concentrations, the ligation mixture is used to transform, for example, ampicillin-sensitive E. coli to ampicillin resistance. Some of the colonies that grow in the presence of ampicillin will contain recombinant plasmids; others will contain plasmid DNA that has recircularized during ligation without insertion of foreign DNA. To discriminate between the two kinds of transformants, a number of colonies are streaked in identical locations on plates containing ampicillin or tetracyclin.

The colonies that survive and grow in the presence of tetracycline contain plasmids with an active tetracycline-resistance gene; such plasmids are unlikely to carry insertions of foreign DNA. The colonies that grow only in the presence of ampicillin contain plasmids with inactive tetracycline-resistance genes; these plasmids are likely to carry foreign DNA sequences.

In a few cases, methods have been developed to apply positive selection to obtain bacteria that are sensitive to an antibiotic from populations that are predominantly resistant. In this way, it is possible to select from recombinant plasmids that carry an inactivated antibiotic-resistance gene as a consequence of insertion of a foreign DNA sequence. The most useful of these systems is that described by Bochner et al (1980) and Maloy and Nunn (1981), who developed media containing the lipophilic, chelating agents fusaric acid or quinaldic acid, which allow the direct positive selection of $Tet^s$ clones from a population of $Tet^s$ and $Tet^r$ bacteria. For most strains of E. coli, approximately 90% of the colonies obtained on media containing tetracycline and fusaric acid were found to be $Tet^s$ when plated onto media containing tetracycline alone. It is, therefore, possible to select from a population of plasmids with insertions at the BamHI and SalI sites.

A similar technique has been developed to select for bacteria sensitive to paromomycin (Slutsky et al, 1980). This should allow the selection of derivatives of pMK16 that contain insertions at the SmaI or XhoI site (Kahn et al, 1979).

Although insertion of foreign DNA sequences within an antibiotic-resistance gene almost always leads to inactivation of that gene, at least one case is known where an insertion left the gene in a functional state. Villa-Komaroff et al (1978) found that insertion of a segment of rat preproinsulin cDNA into the PstI site of pBR322 does not inactivate the ampicillin-resistance gene. Presumably, a small piece of foreign DNA had been inserted that did not alter the reading-frame of the ampicillin-resistance gene, so that a fusion protein was formed which retained beta-lactamase activity.

Directional Cloning

Most plasmid vectors carry two or more unique restriction enzyme recognition sites. For example, the plasmid pBR322 contain single HindIII and BamHI sites.

After cleavage by both enzymes, the larger fragment of plasmid DNA can be purified by gel electrophoresis and ligated to a segment of foreign DNA containing cohesive ends compatible with those generated by BamHI and HindIII. The resulting circular recombinant is then used to transform E. coli to ampicillin resistance. Because of the lack of complemntarity between the HindIII and BamHI protruding ends, the larger vector fragment cannot circularize efficiently; it, therefore, transforms E. coli very poorly. Therefore, most of the colonies resistant to ampicillin contain plasmids that carry foreign DNA segments forming a bridge between the HindIII and BamHI sites. Of course, different combinations of enzymes can be used, depending on the locations of restrictions sites within vector and the segment of foreign DNA.

Phosphatase Treatment of Linear, Plasmid Vector DNA

During ligation, DNA ligase will catalyze the formation of a phosphodiester bond between adjacent nucleotides only if one nucleotide contains a 5'-phosphate group and the other a 3'-hydroxyl group. Recircularization of plasmid DNA can, therefore, be minimized by removing the 5' phosphates from both ends of the linear DNA with bacterial alkaline phosphatase or calf intestinal phosphatase (Seeburg et al, 1977; Ullrich et al, 1977). As a result, neither strand of the duplex can form a phosphodiester bond. However, a foreign DNA segment with 5'-terminal phosphates can be ligated efficiently to the dephosphorylated plasmid DNA to give an open circular molecule containing two nicks.

Because circular DNA (even nicked circular DNA) transforms much more efficiently than linear plasmid DNA, most of the transformants will contain recombinant plasmids. Problems in Cloning Large DNA Fragments in Plasmids.

Finally, the size of the foreign DNA to be inserted can also affect the ratio of transformants containing recombinant plasmids to those containing recircularized vectors. In general, the larger the insertion of foreign DNA,, the lower the efficiency of transformation. Thus, when cloning large DNA fragments (less than 10 kb), it is especially important to take all possible measures to keep the number or recircularized vector molecules to a minimum. Even so, the background is relatively high, and it is usually necessary to use an in situ hybridization procedure (Grunstein and Hogness 1975; Hanahan and Meselson 1980) to identify recombinant transformants.

1. pHW104 is a derivative of pBR322 that has 4–5 copies of the 203 bp Hae III segment of the lac operon that contains the lac repressor binding site. The segment is tailed with Eco RI linkers, and tanden copies are inserted into the $Ap^R Tc^S$ vector pHW1 (a derivative of PBR322 prepared by Hae II digestion to lack the sequence 236 to 2352) at the Eco Ri site.

2. pSS737 is a derivative of pBR322 that has the 737 bp Alu I segment of the human β-globin gene that contains about 0.5 kb of the gene and about 0.25 kb of upstream flanking sequence. The segment is tailed with Eco RI linkers and inserted into the Eco Ri site of pBR322.

The procedure for putting the lac repressor binding sites and the segment of the β-globin gene in the single plasmid as in 1 and 2 above, is as follows:

a. Linearize pHW104 with Hind III; treat with alkaline phosphatase to prevent recirculariztion in step c.

b. Digest pSS737 with Hind III plus Fnu DII; collect the greater than 0.76 kb segment from a preparative agarose gel.

c. Ligate the products of steps a and b, then fill in free Hind III ends using the Klenow fragment of DNA polymerase and deoxyribnucleotide triphosphates.

d. Blunt-end ligate (c) molecules to make circular plasmids, then transform E. coli cells to ampicillin resistance.

e. Collect a number of $Ap^R$ colonies and grow cells for the minilysate production of small amounts of plasmid.

f. Check the plasmids for composition by restriction enzyme digestion. The desired plasmid has:
  i. a single Hind III site;
  ii. Eco RI segments of 2.2, 0.74 and 0.21 kg;
  iii. digestibility by Mst II;
  iv. Desirably a Cla I segment of about 0.75 kb, depending on the orientation of the globin gene insert.

The separation and detection probe for dual hybridization analysis of sickle cell defect are disclosed in detail in application Ser. No. 511,063, filed July 5, 1983, described hereinabove.

3. Use of a plasmid having both multiple copies of the lac repressor binding site and a portion of the β-hemoglobin gene as a hybridization probe:

For the plasmid to be useful probe for the detection of β-globin gene sequence in a simple of DNA, the globin gene portion of the plasmid must be single stranded so that in a subsequent test it can hybridize to a sample of denatured DNA, and the lac operator region must be double stranded to allow binding of the lac repressor protein.

To achieve this, the plasmid product of (2) is linearized using Hind III, then is subjected to a controlled digestion by exonuclease III (λ exonuclease or T4DNA polymerase can be similarly employed). Such treatment makes most or all of the globin gene portion single stranded, leaving most of the rest of the plasmid, including the copies of the lac operator region double stranded.

Alternatively, pairs of pEMBL plasmids (available from the European Molecular Biology Laboratories, Heidelberg) can be used. These plasmids contain a portion of the $F_1$ phage genome, so that they behave like phage M13 in producing single stranded DNA molecules. Unlike with M13, however, it is possible with pEMBL to collect both complementary strands of a plasmid in pure form simply by having the $F_1$ portion of the pEMBL genome in different orientation in two strains; it is the orientation of the $F_1$ genes in the plasmid that determines which of the two strains of the plasmid DNA will be secreted from infected bacteria as single stranded DNA phage.

For example, one plasmid, pEMBL8(+), is engineered to contain tandem copies of the lac repressor binding site plus a portion of the β-hemoglobin gene; another plasmid, pEMBL8(−), contains just the tandem copies of the lac repressor binding site. The single stranded DNA of pEMBL8(+) is hybridized to a sample of unknown DNA, and contact is made through sequence homology between the globin gene portion of the probe and complementary sequences in the sample. The lac operator portion of the probe is made double stranded for lac repressor binding by the annealing of pEMBL8(−) to the pEMBL8(+)-sample DNA complex.

It is possible to carry out such reactions with the replicative (but not the single stranded phage) form of M13 as well as with any plasmid DNA, but one has either to separate the complementary strands, or take considerable loss in hybridization efficiency by having both strands of a plasmid present in a hybridization mixture, where they can undesirably self-anneal.

Step III—(a) Labeling of the Protein with Fluorescein

Fluoresceinisothiocyanate (FITC) is dissolved in ethanol (5 mg solid/ml). To 2 ml of a 5 mg/ml protein solution from (I), 0.5 ml carbonate buffer (1M NaHCO$_3$—Na$_2$CO$_3$ buffer pH 9) is added, followed by 50 μl FITC solution. The mixture is shaken well and the free FITC is chromatographically separated from the bound molecules on a Sephadex G50 column using a buffer comprising 10 mM Tris, 1 mM EDTA, 50 mM KCl, pH 7.4. The labeled protein is collected in the void volume.

(b) Labeling with β-Galactosidase Enzyme

Lac repressor protein from I and β-galactosidase (1:1 molar ratio) (alkaline phosphatase, horseradish peroxidase react similarly) are mixed in phosphate buffer and glutaraldehyde is added to final concentration of 0.2%. Reaction is allowed to proceed for 4 hours. The protein mixture is dialyzed against the same Tris EDTA buffer as in (a).

Step IV—Hybridization and Detection Via Labels on the Lac Repressor

Hybridization is done by fixing the separation probe to a solid support according to the example of application Ser. No. 511,063, supra, using as the detection probe that probe produced in II which carries the non-homologous DNA which is the lac repressor protein binding site. After hybridization, the solid support is washed with BSA solution 1% ω/v in Tris-EDTA buffer as in Example 1, Step III(a), and the lac repressor, labeled as in III(a), (b) or (c), is added. The bound repressor is assayed optically (in the example of fluorescein labeled repressor) or enzymatically (in the example of enzyme labeled repressor).

In patent application Ser. No. 511,063, immobilizing a separation probe and labelling a detector probe are described as follows: Plasmid containing the separation probe, e.g., a subclone of the 0.34 kb Hinf segment of pSS737, is treated with 0.1 m NaOH for 5 minutes, then chilled in ice. The sample is neutralized with an equal volume of 0.1N HCl, 0.9M NaCl, 0.09M Na citrate, then filtered under mild aspiration through a nitrocellulose filter (e.g., BA 85 from Schleicher and Schuell) that had been presoaked in 0.9M NaCl, 0.09M Na citrate (6×SSC; 1×Standard Saline Citrate is 0.15M NaCl, 0.015M Na citrate). The filter is then washed with 6×SSC, then 70% ethanol, and baked under vacuum at 80° C. for a few hours, or with no vacuum at 65° C. overnight. At this point, the filter is ready for hybridization procedures, but it can be stored dry for many months.

The purpose of the alkali treatment of plasmid is to denature the DNA. This renders it both capable of binding to nitrocellulose (native DNA does not) and available for subsequent hybridization with other single-stranded DNA. Neutralization of the denatured DNA solution with acid and the addition of salt (as 6×SSC) facilitate the binding of denatured DNA to nitrocellulose, and the low temperature inhibits reannealing of the plasmid while it is being loaded onto the nitrocellulose. Baking of the filter finally immobilizes the DNA.

Labelling of the detector probe with, for example, $^{32}P$ can be accomplished in several ways, all of which are standard methods: The ends of a plasmid that has been made linear by the action of a restriction endonuclease can be labelled either by a reaction in which polynucleotide kinase adds the terminal phosphate of gamma$^{32}P$-ATP to the 5' end of DNA molecules; by the filing in of recessed 3' ends that are generated by some restriction enzymes, through the use of the use of the large (Klenow) fragment of E. coli DNA polymerase and alpha$^{32}P$-labelled deoxyribonucleoside triphosphates; or by the 3' terminal addition of labelled nucleotides through the action of terminal deoxynucleotidyl transferase. More extensive labelling of a probe can be accomplished using phage $T_4$ DNA polymerase, or by strand replacement DNA synthesis ("nick translation") using E. coli DNA polymerase, labelled triphosphates, and plasmid that has been randomly nicked by deoxyribonuclease 1 to produce numerous synthesis primer sites. Other labelling schemes that do not involve radioactivity are also possible.

EXAMPLE 2

Hybridized probe of Example 1 carrying the lac repressor protein can be assayed immunochemically as follows:

(a) Purified lac repressor protein from Example 1 is mixed 1:1 with Freund's complete adjuvant and injected into mice (25 μg protein into both hind foot pads) or rabbits (500 μg subcutaneously). One month later the polyclonal antibody response is titered and the antiserum from animals with strong responses is collected and used for the immunoassays.

(b) To the hybrid complex containing the lac repressor protein of Example 1, specific dilutions of the antiserum of (a) are incubated for 1 hour at room temperature. Unbound antibodies are washed 3 times with a buffer solution comprising 5 mM $NaH_2PO_4$, 150 mM NaCl (pH 7.4) and 0.04% Triton X-100. Protein A covalently coupled to horseradish peroxidase (Sigma Chemical Co. p 8651) diluted 1:8000 in PBS as above, is incubated with the hybridization complex of Example 1 for 30 minutes at room temperature and washed 3 times with the aforementioned buffer. The substrate o-phenylenediamine in citrate buffer containing $H_2O_2$, pH 5.6, is added and the enzymatic reaction product is measured at 492 nm. The amount of bound repressor is determined by comparison to standard quantitation curves.

EXAMPLE 3

The double stranded portion of the detection probe of Example 1 can be modified to bind a specific antibody as follows:

The detection probe is dissolved in 10 mM Tris 1 mM EDTA buffer and mixed with biotin-psoralen adduct as described in Example 1 of application Ser. No. 513,932, supra. The mixture is irradiated with 360 nm light at room temperature for 40 minutes. After the reaction, the sample is dialyzed against the hybridization buffer of Example 1, to exclude unreacted biotin-psoralen adduct.

The biotin-containing detection probe is then hybridized as in Step IV and the hybrid is assayed for the presence of biotin in known manner employing FITC-labelled avidin.

Example 1 of Ser. No. 513,932 describes that 50 mg of N-hydroxysuccinimido biotin is dissolved in 2 ml dimethylsulfoxide (soln A). 10 mg of 4' aminomethyl trioxsalen (structure 1) (or other aminoalxyl compounds) is dissolved in 10 ml (soln B) aqueous buffer solution pH approximately 8. Solutions (A) and (B) are mixed in a volume ratio of 1:10 and weight ratio of 10:1, so that the activated hapten is present in large excess. The reaction is allowed to proceed at 35+ C. for 1 hour. The extent of the reaction is monitored by thin layer chromatography—on silica gel plates with a fluorescence indicator in a solvent 1/1/8—methanol/acetic acid/chloroform. Under these TLC conditions unreacted aminomethyl trioxalane moves with the solvent front, whereas the product has a slower mobility. Biotin does not show any fluorescence but the adduct fluoreces because of trioxsalen. Growth of the new fluorescent spot and disappearance of the original fluorescent spot indicates the extent of product formation. Since the activated biotin is in large excess, fluorescence corresponding to the starting material vanishes on TLC after the completion of reaction. Excess active biotin is reacted with glycidyl-glycine or lysine.

EXAMPLE 4

Introduction of an Antigenic Site into Double Stranded Nucleic Acid by Intercalation Covalent ethidium-DNA complexes are prepared as follows: About 250 mg of salmon sperum DNA (Sigma Chemical Co., St. Louis, MO) is dissolved in 40 ml of 50 nM $ZnCl_2$ and sheared by five passages through a 23 gauge needle. The sheared DNA is placed in a 250 ml flask and diluted with an additional 160 ml of buffer. One hundred forty-five microliters (145 μl) of $S_1$-nuclease, 200,000 units per ml (Pharmacia P-L Biochemicals, Piscataway, NJ), is added and the mixture is incubated at 37° C. for 50 minutes.

Then the reaction mixture is extracted twice with phenol:chloroform, once with chloroform and the DNA is precipitated twice with ethanol [Maniatis et al (1982) "Molecular Cloning", Cold Spring Harbor Laboratory, Cold Spring Harbor, NY]. The final precipitate is dissolved in 70 ml of 20 mM Tris hydrochloride buffer, pH 8.0.

This DNA is reacted with 8-azidoethidium under the following conditions. The reaction mixture is prepared with 33 ml of 2.7 mg DNA/ml, 13.5 ml of 4.95 mM 8-azidoethidium, 13.5 ml of 0.2M Tris-hydrochloride buffer, pH 8.0, 2M NaCl, and 76 ml water. The mixture is placed in a 250 ml beaker with a water jacket maintained at 22° C. The mixture is stirred and illuminated for 60 minutes by a 150 watt spotlight at a distance of 10 cm. This photolysis is repeated with an identical reaction mixture.

The photolyzed reaction mixtures are combined and extracted 10-times with an equal volume each time of n-butanol saturated with 20 mM Tris-hydrochloride buffer, pH 8.0, 0.2M NaCl. The extracted DNA solution is combined with 23 ml of 4.95 mM 8-azidoethidium and 77 ml of 20 mM Tris-hydrochloride buffer, pH 8.0, 0.2M NaCl. This solution is stirred in the water-jacketed beaker and photolyzed for 90 minutes. The reaction products are extracted 10 times with buffer saturated butanol as described above and the DNA is precipitated with ethanol. The precipitate is dissolved in 10 mM Tris-hydrochloride buffer, pH 8.0, 1 mM EDTA and the absorbances at 260 and 490 nm are recorded. Calculations made es described in Example 1A above indicate 1 ethidium residue is incorporated per 4.5 DNA base pairs.

Methylated thryroglobulin is prepared as follows: One hundred milligrams of bovine thryroglobulin (Sigma Chemical Co., St. Louis, MO) is combined with 10 ml of anhydrous methanol and 400 μl of 2.55M HCl in methanol. This mixture is stirred on a rotary mixer at room temperature for 5 days. The precipitate is collected by centrifugation and washed twice with methanol and twice with ethanol. Then it is dried under vacuum overnight. About 82 mg of dry powder is obtained.

Antiserum to covalent ethidium-DNA is titered by an enzyme label immunosorbant assay. Polynucleotides are adsorbed onto the walls of polystyrene microtiter plates and then the rabbit antibody is allowed to bind. Finally the antibody is detected with peroxidase labeled goat anti-rabbit IgG.

Fifty microliter (50 μl) aliquots of solutions containing 5 μg of polynucleotide per ml in 15 mM sodium citrate, pH 7.0, 0.15M NaCl is dispensed into wells of Immulon II microtiter plates (Dynatek, Alexandria, VA) and shaken gently at room temperature for 2 hours. Then the wells are emptied and washed with 10 mM sodium phosphate buffer, pH 7.4, 0.15M NaCl, 0.5% bovine serum albumin and 0.5% Tween 20 (PBS/BSA/Tween).

Rabbit antiserum is diluted into 10 mM sodium phosphate, pH 7.4, 0.15M NaCl, 0.5% BSA and 50 μl aliquots are added to the wells and allowed to stand for 30 minutes. The wells are washed three times with PBS/BSA/Tween. Peroxidase covalently coupled to goat-antirabbit IgG (Cappel Laboratories, Cochranville, PA) is diluted 500-fold in 10 mM sodium phosphate, pH 7.4, 0.15M NaCl, 0.5% BSA and 50 μl aliquots are added to each well. This solution is allowed to stand in the wells for 30 minutes at room temperature and then the wells are washed three times with PBS/BSA/Tween.

On hundred micromolar (100 μM) ethidium bromide is included in the diluted antiserum of wells containing noncovalent ethidium-DNA complex and the ethidium control wells. All wash solutions and reagents described above for processing these wells contain 100 μM ethidium.

A peroxidase substrate solution is prepared with:
20 mg o-phenylenediamine
5 ml 0.5M NaHPO$_4$
12 ml 0.1M sodium citrate
13 ml water
20 μl 30% hydrogen peroxide Seventy-five microliters (75 μl) of substrate solution is added per well and allowed to react for 10 minutes at room temperature. The reactions are quenched by addition of 50 μl of 2.5M sulfuric acid. Then the absorbances at 488 nm are recorded with a Artek Model 210 microliter plate photometer (Dynatek, Alexandria, VA).

Normal rabbit serum is used as a control and is processed as described for the rabbit antiserum The results are given in Table A and show that antibody in the control rabbit serum does not bind at significant levels to any of the coated or uncoated wells. It might have a weak antibody titer to single stranded DNA.

The antiserum to the covalent ethidium-DNA has very high titer to the covalent ethidium-DNA. Part of these antibodies are probably binding to ethidium residues that are coupled covalently to the phosphate ribose chain. This conclusion is based on the observation that the titers to the noncovalent ethidium-DNA complex are much lower (see Table A).

These results demonstrate that antibodies can be raised to the ethidium-DNA intercalation complex which do not crossreact significantly with native single or double stranded nucleic acid.

TABLE A

| Dilution | Absorbances (488 nm) | | | | | |
|---|---|---|---|---|---|---|
| | Buffer Control | Covalent Ethidium-DNA | Double-strand DNA | Noncovalent Ethidium-DNA | Ethidium Control | Single-strand DNA |
| Antiserum | | | | | | |
| 50 | 0.067 | 1.2 | 0.126 | 0.825 | 0.049 | 0.283 |
| 200 | 0.032 | 1.2 | 0.068 | 0.597 | 0.021 | 0.184 |
| 800 | 0.022 | 1.2 | 0.067 | 0.30 | 0.016 | 0.174 |
| Control Serum | | | | | | |
| 50 | 0.038 | 0.053 | 0.091 | 0.031 | 0.023 | 0.245 |
| 200 | 0.025 | 0.044 | 0.082 | 0.016 | 0.017 | 0.181 |
| 800 | 0.017 | 0.034 | 0.054 | 0.015 | 0.016 | 0.190 |

Notes:
(1) The buffer control does not contain DNA on the wells.
(2) Double-stranded DNA contains calf thymus DNA on the wells.
(3) Noncovalent ethidium-DNA has calf thymus double-stranded DNA on the wells and 100 μM ethidium in the reagent and wash solutions.
(4) Ethidium control does not have DNA on the wells but has 100 μM ethidium in the reagent and wash solutions.
(5) The single-stranded DNA has heat denatured calf thymus DNA coated on the wells.

It is understood that the specification and examples are illustrative, but not limiting to the present invention and that other embodiments within the spirit and scope of the invention will suggest themselves to those skilled in the art.

What is claimed is:

1. A nucleic acid detection probe comprising a hybridizable single stranded portion of nucleic acid connected with a non-hybridizable, single stranded nucleic acid portion, the non-hybridizable portion including a recognition site for binding by a particular protein, wherein the non-hybridizable portion has been modified to create the protein recognition site and wherein the modification is effected by connecting to said non-hybridizable portion an intercalating agent or wherein the modification is effected by contact with a modifier compound which introduces an antigenic determinant into the non-hybridizable portion.

2. A detection probe according to claim 1, wherein the hybridizable portion is covalently linked to the non-hybridizable portion.

3. A detection probe according to claim 1, wherein the hybridizable portion is complementary to the genomic sequence responsible for sickle cell anemia.

4. A detection probe according to claim 1, wherein the non-hybridizable portion comprises single stranded nucleic acid photochemically linked with an intercalating agent.

5. A detection probe according to claim 1, wherein the modifier compound is an intercalating agent selected from the group consisting of acridine dyes, phenazines, phenothiazines, and quinolines.

6. A detection probe according to claim 1, including the particular protein bound to the protein-specific site of the non-hybridizable portion.

7. A detection probe according to claim 6, wherein the protein carries a label.

8. A detection probe according to claim 7, wherein the label is selected from the group consisting of a fluorescer, a chromophore, a luminescer, a specifically bindable ligand and a radioisotope.

9. A detection probe according to claim 1, including a labeled from of the particular protein bound to the protein-specific site of the non-hybridizable portion, wherein the labeled protein comprises a protein selected from the group consisting of an antibody, and an antibody fragment and a label selected from the group consisting of an enzymatically active group, a fluorescer, a chromophore, a liminescer, a specifically bindable ligand and a radioisotope.

10. A method for detecting a particular polynucleotide sequence in a test medium containing single stranded nucleic acids, comprising the steps of:
(a) combining a test medium with a nucleic acid detection probe comprising at least one hybridizable single stranded base sequence to be detected and a non-hybridizable double-stranded portion having a recognition site for binding by a particular protein, under conditions favorable to hybridization between the sequence to be detected and the complementary hybridizable sequence in the probe, wherein the non-hybridizable portion has been modified to create the protein recognition site, wherein the modification is effected by connecting to said non-hybridizable portion an intercalating agent or a platinum-containing ligand or the modification is effected by introducing an antigenic determinant into the non-hybridizable portion,
(b) separating hybridized probe from unhybridized probe, and
(c) adding to the separated hybridized probe, the particular protein which binds the recognition site on the non-hybridizable portion of the probe and determining the protein which becomes bound to the solid support.

11. A method according to claim 10 which is a solid phase hybridization technique, wherein the single stranded nucleic acids from the test medium are immobilized on a solid support and wherein the protein associated with the solid support is determined.

12. A method according to claim 10 which is a solid phase sandwich hybridization technique, wherein the test medium is combined with first and second nucleic acid probes each comprising at least one hybridizable single stranded base sequence which is substantially complementary to a mutually exclusive portion of the sequence to be detected and wherein one of the probes is immobilized on a solid support and the other has said non-hybridizable portion having said protein recognition site.

13. A method according to claim 10, wherein the non-hybridizable portion comprises single stranded nucleic acid photochemically linked with an intercalating agent.

14. A method according to claim 10, wherein the non-hybridizable portion comprises double stranded nucleic acid in the form of intercalating complexes with an intercalating agent.

15. A method according to claim 14, wherein the intercalating agent is covalently linked to at least one of the two strands of the double stranded portion.

16. A method according to claim 10, wherein the modification is effected by contact with a modifier compound, said modifier compound being an intercalating agent selected from the group consisting of acaridine dyes, phenanthridines, phenazines, furocouramarins, phenothiazines and quinolines.

17. A method according to claim 10, wherein the non-hybridizable portion has been modified by contact with a salt.

18. A method according to claim 10, wherein the particular protein carries a label.

19. A method according to claim 18, wherein the label is selected from the group consisting of an enzymatically active group, a fluorescer, a chromophore, a luminescer, a specifically bindable ligand and a radioisotope.

20. A method according to claim 10, wherein the protein is an antibody, or a fragment thereof, labeled with a label selected from the group consisting of an enzymatically active group, a fluorescer, a chromophore, a luminescer, a specifically bindable ligand and a radioisotope.

21. A kit for detecting a particular polynucleotide sequence in a test medium, comprising in one or more containers:
(1) a nucleic acid detection probe according to claim 1, and
(2) a particular protein capable of binding to the recognition site or the detection probe.

22. A kit according to claim 21, wherein the non-hybridizable portion comprises single stranded nucleic acid photochemically linked with an intercalating agent.

23. A kit according to claim 21, wherein the non-hybridizable portion comprises double stranded nucleic acid in the form of intercalating complexes with an intercalating agent.

24. A kit according to claim 23, wherein the intercalating agent is covalently linked to at least one of the two strands of the double stranded portion.

25. A kit according to claim 21, wherein the modifier compound is an intercalating agent selected from the group consisting of acridine dyes, phenazines, phenothiazines and quinolines.

26. A kit according to claim 21, wherein the particular protein carries a label.

27. A kit according to claim 26, wherein the label is selected from the group consisting of an enzymatically active group, a fluorescer, a chromophor, a luminescer, a specifically bindable ligand and a radioisotope.

28. A kit according to claim 21, wherein the protein is an antibody, or a fragment thereof, labeled with a label selected from the group consisting of an enzymatically active group, a fluorescer, a chromophore, a luminescer, a specifically bindable ligand and a radioisotype.

29. An antibody, or fragment thereof, capable of binding with an intercalation complex formed between double stranded nucleic acid and a nucleic acid.

30. The antibody or fragment thereof of claim 29 which is incapable of binding to single stranded nucleic acids.

31. An antibody or fragment thereof of claim 29 wherein the intercalator is selected from the group consisting of acridine dyes, phenazines, phenothiazines and quinolines.

32. The antibody or fragment thereof of claim 29 wherein the double stranded nucleic acid is a DNA/DNA duplex.

33. The antibody or fragment thereof of claim 29 which is labeled with a detectable chemical group.

34. An antibody or fragment thereof of claim 33 wherein the detectable chemical group is selected from the group consisting of an enzymatically active group, a fluorescer, a chromophore, a luminescer, a specifically bindable ligand and a radioisotope.

35. A nucleic acid detection probe comprising a hybridizable single stranded portion of nucleic acid connected with a non-hybridizable, double stranded nucleic acid portion, the non-hybridizable portion including a recognition site for binding by a particular protein, wherein the non-hybridizable portion has been modified to create the protein recognition site and wherein the modification is effected by connecting to said non-hybridizable portion an intercalating agent or wherein the modification is effected by contact with a modifier compound which introduces an antigenic determinant into the non-hybridizable portion.

36. A detection probe according to claim 35, wherein the hybridizable portion is covalently linked with one of the strands of the non-hybridizable portion.

37. A detection probes according to claim 35, wherein the hybridizable portion is complementary to the genomic sequence responsible for sickle cell anemia.

38. A detection probe according to claim 35, wherein the non-hybridizable portion comprises single stranded nucleic acid photochemically linked with an intercalating agent.

39. A detection probe according to claim 35, wherein the non-hybridizable portion comprises double stranded nucleic acid in the form of intercalating complexes with an intercalating agent.

40. A detection probe according to claim 39, wherein the intercalating agent is covalently linked to at least one of the two strands of the double stranded portion.

41. A detection probe according to claim 35, wherein the modifier compound is an intercalating agent selected from the group conisting of acridine dyes, phenazines, phenothiazines and quinolines.

42. A detection probe according to claim 35, including the particular protein bound to the protein-specific site of the non-hybridizable portion.

43. A detection probe according to claim 42, wherein the protein carries a label.

44. A detection probe according to claim 43, wherein the label is selected from the group consisting of an enzymatically active group, a fluorescer, a chromophore, a luminescer, a specifically bindable ligand and a radioisotope.

45. A detection probe according to claim 35, including a labeled from of the particular protein bound to the protein-specific site of the non-hybridizable portion, wherein the labeled protein is an antibody, or a fragment thereof, labeled with a label selected from the group consisting of an enzymatically active group, a fluorescer, a chromophore, a luminescer, a specifically bindable ligand and a radioisotope.

* * * * *

UNITED STATES PATENT AND TRADEMARK OFFICE
CERTIFICATE OF CORRECTION

PATENT NO. : 4,777,129
DATED : Oct. 11, 1988
INVENTOR(S) : Dattagupta et al.

It is certified that error appears in the above-identified patent and that said Letters Patent is hereby corrected as shown below:

| | |
|---|---|
| Col. 8, Line 9 | Delete "re" and substitute --are-- |
| Col. 12, Line 55 | Correct spelling of --microcapsule-- |
| Col. 14, Line 21 | Delete "-" after "time" |
| Col. 16, Line 65 | Delete "recirculated" and substitute --recircularized-- |
| Col. 18, Lines 38 and 39 | Delete "Problems in Cloning Large DNA Fragments in Plasmids." and substitute said sentence, without period, on next line as a heading |
| Col. 26, Line 58 | Delete "21" and substitute --25-- |
| Col. 28, Line 30 | Delete "from" and substitute --form-- |

Signed and Sealed this

Twenty-fifth Day of July, 1989

Attest:

DONALD J. QUIGG

Attesting Officer

Commissioner of Patents and Trademarks